(12) United States Patent
Berge (10) Patent No.: US 8,545,555 B2
(45) Date of Patent: Oct. 1, 2013

(54) ELECTRONICALLY CONTROLLED FOCUSING OPHTHALMIC DEVICE

(75) Inventor: Bruno Berge, Lyons (FR)

(73) Assignee: Parrot, Paris (FR)

( * ) Notice: Subject to any disclaimer, the term of this patent is extended or adjusted under 35 U.S.C. 154(b) by 0 days.

(21) Appl. No.: 13/513,678

(22) PCT Filed: Dec. 3, 2010

(86) PCT No.: PCT/EP2010/068878
§ 371 (c)(1),
(2), (4) Date: Aug. 17, 2012

(87) PCT Pub. No.: WO2011/067391
PCT Pub. Date: Jun. 9, 2011

(65) Prior Publication Data
US 2012/0310339 A1 Dec. 6, 2012

(51) Int. Cl.
*A61F 2/16* (2006.01)

(52) U.S. Cl.
USPC ............ 623/6.22; 623/6.13; 623/24; 359/227

(58) Field of Classification Search
USPC .......................... 623/6.13, 6.22; 351/41, 168
See application file for complete search history.

(56) References Cited

FOREIGN PATENT DOCUMENTS

| EP | 1 870 741 A1 | 12/2007 |
|---|---|---|
| EP | 1 906 214 A1 | 4/2008 |
| EP | 1996968 A1 | 12/2008 |
| WO | 2004/004605 A1 | 1/2004 |
| WO | 2007/088453 A1 | 8/2007 |
| WO | 2007/107589 A1 | 9/2007 |

OTHER PUBLICATIONS

International Search Report issued in PCT/EP2010/068878, mailed on Feb. 25, 2011, 2 pages.
Written Opinion issued in PCT/EP2010/068878, mailed on Feb. 25, 2011, 3 pages.

*Primary Examiner* — William H Matthews
(74) *Attorney, Agent, or Firm* — Osha Liang LLP (57) ABSTRACT

According to a first aspect, the invention relates to an electrically controlled focusing ophthalmic device (43) to be worn by a user, comprising:—at least one active liquid lens comprising a liquid/liquid interface movable by electrowetting under the application of a voltage,—a driver for applying a DC voltage to said active liquid lens, the amplitude of the voltage to be applied being a function of the desired focusing;—a sensor (41) for detecting eyelid closing events and/or microsaccades of the user;—a controller for synchronizing said sensor and the driver, such that the driver may reverse the polarization of the DC voltage during a microsaccade and/or an eyelid closing event of the user.

13 Claims, 5 Drawing Sheets

ELECTRONICALLY CONTROLLED FOCUSING OPHTHALMIC DEVICE

BACKGROUND

1. Field of the Disclosure

The invention relates to an electronically controlled focusing ophthalmic device, and more particularly to an automatic focusing ophthalmic device for the treatment of accommodation disorders, such as presbyopia. Such ophthalmic devices are for example eyeglasses, contact lenses or intra ocular implants.

2. Background Art

Presbyopia is a condition where the eye exhibits a progressively diminished ability to focus on near objects with age. Another situation where people are loosing accomodation is after a cataract surgery; following surgical removal of the natural lens, an artificial intraocular lens implant is inserted, which is a fixed focal lens made of a transparent polymer. Corrective lenses and contact lenses have been largely developed to correct the focusing loss that comes along with presbyopia and other accomodation disorders. More recently, implantation of accommodative intraocular lenses (IOLs) has been developed.

Figure 1A:
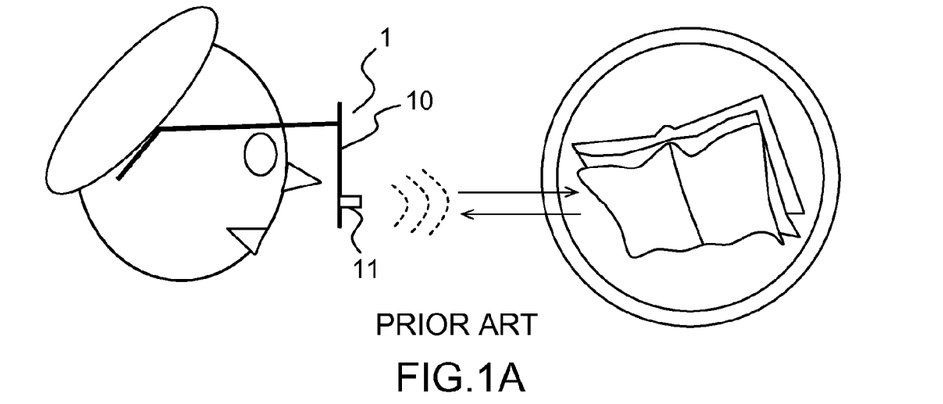
FIGS. 1A and 1B (already described), a general configuration for an electrically controlled focusing ophthalmic device and spectacles according to the prior art.

Automatic focusing lenses or automatic focusing implants may bring automatic accommodation, which is a very important feature for the treatment of presbyopia or other accommodation disorders. Automatic accommodation is the ability for the eye to automatically focus on the observed scene, producing a sharp image on the retina, whatever the distance of the object is. FIG. 1A illustrates the general configuration for an automatic focusing lens vision system, for correcting presbyopia. The patient wears glasses 1 with active lenses 10, said active lenses 10 having a variable optical dioptric correction depending on the measured distance of an object that the patient is looking at by a rangefinder 11, said rangefinder being for example fixed on the glasses.

One difficulty for automatic focusing lenses (especially for the contact lenses and for the intraocular implants) is to provide the control signal to the lens comprising the distance information on the object that the patient is looking at.

Another difficulty for an automatic focusing lens is to provide a suitable small battery or any other power source that allows the lens to be operated. Due to the limited space available on contact lenses or intraocular implants, the available power consumption of the automatic focusing lens will be limited to very small power consumption, typically in the order of a few microwatts. For eyeglasses, the limit of weight of the glasses also brings a constraint on the battery type, which results in the same goal of achieving an automatic focusing lens consuming no more than a few microwatts or even tens of nanowatts.

Figure 1B:
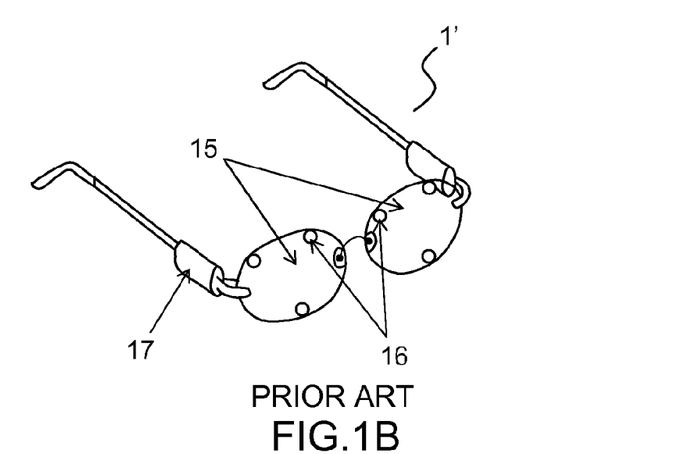

Some prior art publications (see for example Syu Sato et al. Journal of Robotics and Mechatronics Vol.13 No.6, 2001, 581-586 and Toyomi Fujita et al., Journal of Robotics and Mechatronics Vol.13 No.6, 575-579) describe vision systems with automatic focusing lenses using deformable lenses, wherein the rangefinder is made with a small optical device measuring the eyes convergence. FIG. 1B shows automatic focusing eyeglasses 1' described in the cited publication from Toyomi Fujita et al. The glasses comprise variable focusing lenses 15, controlled by a focal length lens driver 17. Gaze distance detectors 16 are implemented on the glasses to measure the convergence of the eye and calculate the corresponding distance of the object the patient is looking at.

Different types of deformable lenses are known in the art. Liquid crystal based adaptive lenses for intraocular implants have been described for example in Vdovin et al. (Optics Express, voll no7 (2003) pp 810-81). In G. Li et al. (Proc. Natl. Acad. Sci. USA, 2006 103 p 6100), it is shown a pair of spectacles comprising variable diffractive lenses.

Figure 2:
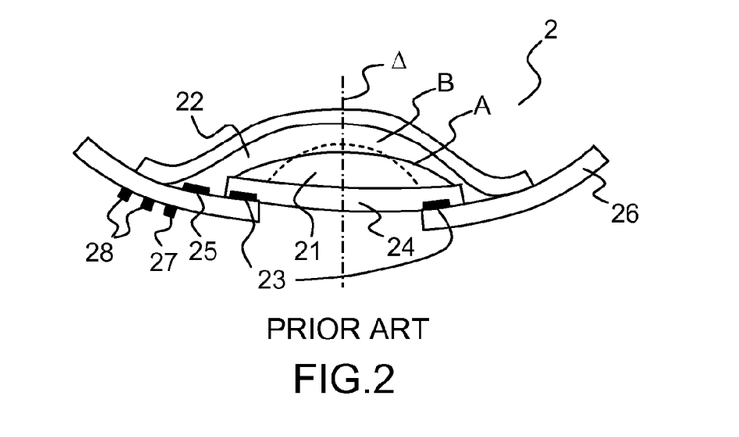
FIG. 2 (already described), an electrowetting based active lens implemented in an intraocular implant according to the prior art.

European patent application no EP1996968 in the name of the applicant describes a variable focusing implant based on electrowetting, a figure of which is reproduced on FIG. 2. Among others, electrowetting-based active liquid lenses bring a high correction dynamics compared to other technologies, such as crystal liquid active lenses for example. For example, a typical range of optical variation of 5 to 7 diopters can be achieved with a 6 mm pupil diameter liquid lens. The implant 2 comprises a capsule 2 made of a transparent and flexible material, for example a transparent polymer like PMMA, polycarbonate, epoxies, polyesters, fluoropolymers, FEP, PTFA, polyolefins, or polycycloolefins. Inside the capsule, two liquids 21, 22 are trapped, which are transparent, non miscible, have approximately the same density and have different indices of refraction. The first liquid 21 is a non-polar liquid, non conducting (or insulating liquid) forming a drop inside the capsule. The second liquid 22 is a conducting polar liquid; it can be a water based solution. A first electrode 23 having a ring shape is covered with a thin insulator film 24 for electrowetting actuation. In the arrangement as shown on FIG. 2, the thin insulator film 24 is also playing the role of the capsule window. A second electrode 25 is in direct contact with the conducting liquid 22. Electrowetting actuation is used to activate the lens. Upon a control signal, a voltage is applied between the electrodes 23 and 25. The applied voltage induces via an electrowetting effect a change in the contact angle of the drop of liquid 21. As shown on FIG. 2, the shape of the drop changes from shape A (flat drop) to shape B (curved drop) while the voltage varies. As the indices of refraction of the two liquids are different, the device forms a variable power lens whose dioptric variation can range from a few diopters to several tens of diopters.

It has been shown that the variation of the contact angle with voltage is theoretically proportional to the square of the applied voltage (see for example B. Berge, "Electrocapillarity and wetting of insulator films by water" Comptes rendus de l'Académie des sciences—Serie deux, Mécanique, physique, chimie, sciences de l'univers, sciences de la terre—ISSN 0764-4450—1993, vol. 317, no2, pp. 157-163). The contact angle $\theta$ can be expressed as a function of the voltage V by the formula:

$$\cos\theta = \cos\theta_0 + \frac{\varepsilon\varepsilon_0}{2e\gamma}V^2 \qquad (1)$$

where $\varepsilon, \varepsilon_0, \gamma$ are respectively the dielectric constant of the insulator film, the dielectric constant of the vacuum and the interfacial tension of the two liquids interface.

Thus, the electrowetting effect can theoretically be obtained by a DC voltage (either positive or negative), or by an AC voltage, the voltage V in equation (1) being replaced by its RMS (root mean square) value:

$$V_{rms} = \sqrt{\langle V^2 \rangle}$$

The applicant has shown that both solutions may be used to make an automatic focusing lens based on electrowetting. Using AC voltage may result in a very stable automatic focusing lens, wherein the optical power correction (dioptric correction) is very stable with time. But the power consumption is high (typically a few tens of mW). Using DC voltages may allow a low power consumption as there is no need for producing current for voltage reversal. However, the dioptric correction may not be stable with time, as explained below.

Figure 3A:
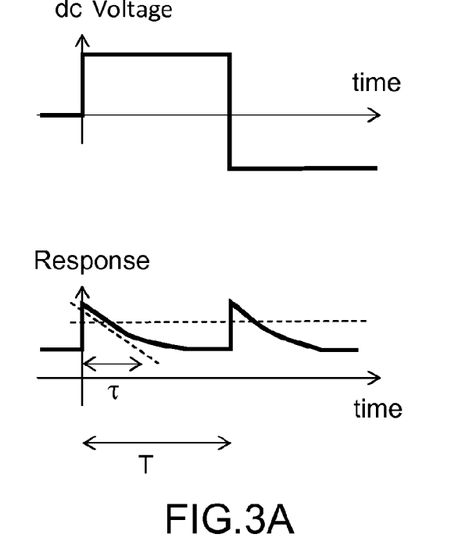
FIGS. 3A and 3B (already described), responses of an electrowetting based active lens in function of an applied voltage in two configurations.
Figure 3B:
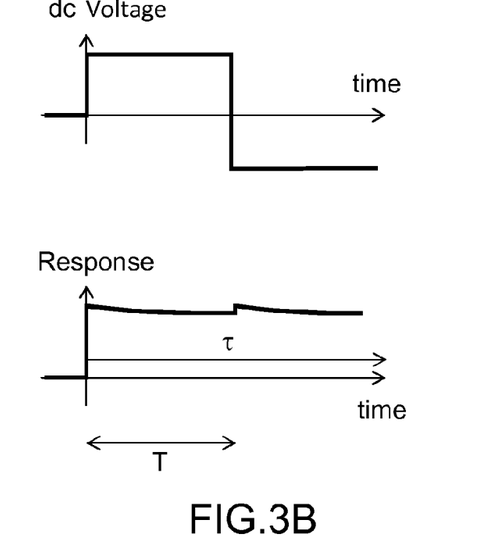

As shown on FIGS. 3A and 3B, when a constant voltage is applied, the electrowetting effect slowly decreases with a time constant $\tau$ ranging from tens of milliseconds to hundreds of seconds. When the correction is applied for very long times (tens of minutes), ultimately the electrowetting effect completely vanishes. Upon polarization reversal, the electrowetting effect is restored inducing a perturbation in the vision of the patient. FIGS. 3A and 3B show typical responses of an electrowetting based active lens driven by DC voltage. On top of each figure is shown the DC voltage applied to the active lens as a function of time. For each example, a polarization reversal is applied with an half period T. On the bottom of each figure is shown the electrowetting response in arbitrary units. The electrowetting response may be either the contact angle, the lens optical power in diopters, or any other direct or indirect measurement of the liquid drop shape, as for example its capacitance. In the example of FIG. 3A, the time constant $\tau$ of the electrowetting effect is much smaller than the half period T resulting in the decreasing of the electrowetting effect until it vanishes. FIG. 3B shows the opposite case where the time constant $\tau$ of the electrowetting effect is much larger than the half period T. Even in this case, there may be a discontinuity in the electrowetting effect which may be visible for the patient as a little shock perturbation. This perturbation can be annoying or even unbearable.

One object of the present invention is to provide an electronically controlled ophthalmic device, e.g. for correction of presbyopia or other accommodation disorders, with low electrical power consumption while keeping a very stable optical correction.

SUMMARY OF THE INVENTION

According to a first aspect, the invention relates to a method for controlling an electrically controlled focusing ophthalmic device worn by a user, said device comprising at least one active lens comprising a liquid/liquid interface movable by electrowetting under the application of a voltage, said method comprising:
   applying a DC voltage to said active lens, the amplitude of the voltage being a function of the desired focusing of the ophthalmic device;
   detecting a microsaccade and/or eyelid closing event of the user;
   reversing the polarization of the DC voltage during said microsaccade and/or eyelid closing event.

Taking advantage of a microsaccade or eyelid closing event to reverse the polarization enables to make an eventual discontinuity in the electrowetting effect while reversing the polarization invisible for the patient (user).

According to a preferred embodiment, the method further comprises measuring the elapsed time since the last polarization reversal of the voltage and reversing the polarization of the DC voltage only when said elapsed time is larger than a given first value. The measurement of the elapsed time since the last polarization reversal enables to make it sure that the polarization reversal won't be made to often, thus keeping the power consumption low.

Typically, said first value is comprised between about 100 ms and 10 s, for example between 1 s and 5 s. Said first value is for example determined as a function of the maximal power consumption tolerated by the system.

According to a further preferred embodiment, the method further comprises reversing the polarization of the DC voltage during the next detected microsaccade or eyelid closing event of the user when said elapsed time is larger than said first value and smaller than a given second value; and reversing the polarization of the DC voltage as soon as said elapsed time is larger than said second value. This enables to ensure that a polarization reversal will be made after a given (maximal) time even if there is no microsaccade or eyelid closing event by the user, thus preventing any substantial decrease in the electrowetting effect.

Typically, said second value is comprised between about 10 s and 2 min, and may be determined in function of the electrowetting time constant of the liquid lens.

According to a further preferred embodiment, the method further comprises measuring the distance of an object the user is looking at to determine the desired focusing. It enables to make an automatically control the active liquid lens, based on the measured distance.

According to a second aspect, the invention relates to an electrically controlled focusing ophthalmic device to be worn by a user, comprising:
   At least one active liquid lens comprising a liquid/liquid interface movable by electrowetting under the application of a voltage,
   a driver for applying a DC voltage to said active liquid lens, the amplitude of the voltage to be applied being a function of the desired focusing;
   a sensor for detecting eyelid closing events and/or microsaccades of the user;
   a controller for synchronizing said sensor and the driver, such that the driver may reverse the polarization of the DC voltage during a microsaccade and/or an eyelid closing event of the user.

According to a preferred embodiment, the ophthalmic device further comprises a device for measuring the distance of an object the user is looking at, the desired focusing being function of the measured distance.

According to a further preferred embodiment, the controller is further adapted for measuring the elapsed time since the last polarization reversal.

According to a preferred embodiment, the active lens comprises:
   a chamber containing two transparent non miscible liquids forming said liquid/liquid interface, a first electrically conducting liquid and a second non conducting liquid,
   a first electrode covered with an insulator film and a second electrode in contact with said electrically conducting liquid, the DC voltage being applied to said electrodes.

According to a preferred embodiment, the time constant of the electrowetting effect is larger that 1 s. Having large time constants for the electrowetting effect enables to limit the residual shock perturbation for the user when a polarization reversal is made outside an eyelid closing event or a microsaccade.

According to a first example, the electrically controlled focusing ophthalmic device is an intra ocular implant or a contact lens.

According to a second example, the electrically controlled focusing ophthalmic device is a pair of eyeglasses comprising two active liquid lenses and a driver for each active liquid lens, the controller further ensuring the synchronization between said sensor and the drivers.

BRIEF DESCRIPTION OF DRAWINGS

Other aspects and advantages of the invention will be apparent from the following description, illustrated by the following figures.

DETAILED DESCRIPTION

Figure 4:
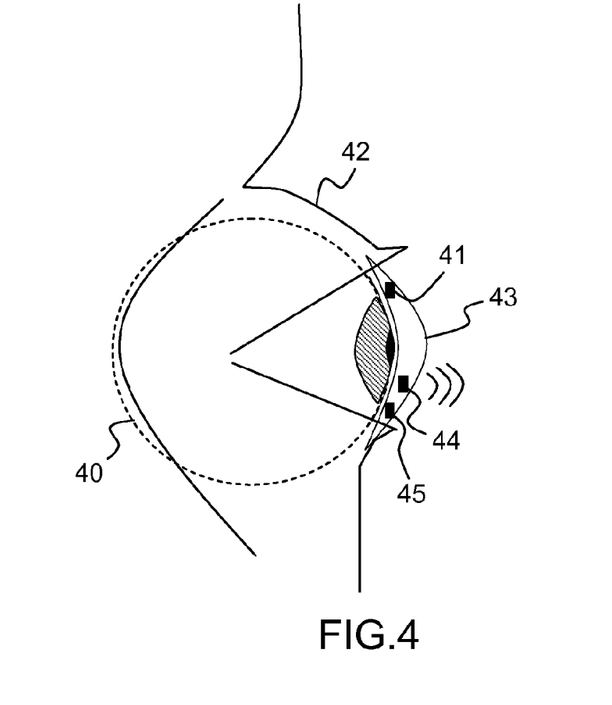
FIG. 4, an example of an electronically controlled ophthalmic device according to an embodiment of the invention.

FIG. 4 shows an example of an electrically controlled focusing ophthalmic device according to a first preferred embodiment. The device comprises an active contact lens 43 to be placed on the eye 40 of a patient and comprising a liquid/liquid interface (not shown on FIG. 4) actuated by electrowetting, thus forming an active liquid lens. It further comprises a distance measuring device 44 for measuring the distance of an object to be focused on. For example, the range meter is a sensor enabling the measurement of the eye convergence of the user as described in the prior art. The device also comprises an electronic module 45 with a power supply, a driver for the liquid lens and a controller. The driver is adapted to apply to the liquid lens a voltage dependent on the desired focusing. The desired focusing may be calculated from the distance of an object measured by the distance measuring device 44, thus making an automatic focusing of the device. Reversal of the polarization of the voltage is achieved to restore the electrowetting effect as it will be explained in more details below. In the embodiment as shown on FIG. 4, the ophthalmic device further comprises an eyelid sensor 41 for detecting when the eyelid 42 of the user is closing.

According to a preferred embodiment, synchronizing the polarization reversal with an eyelid closing event (first mode) and/or with an eye microsaccade (second mode) is performed.

Figure 5:
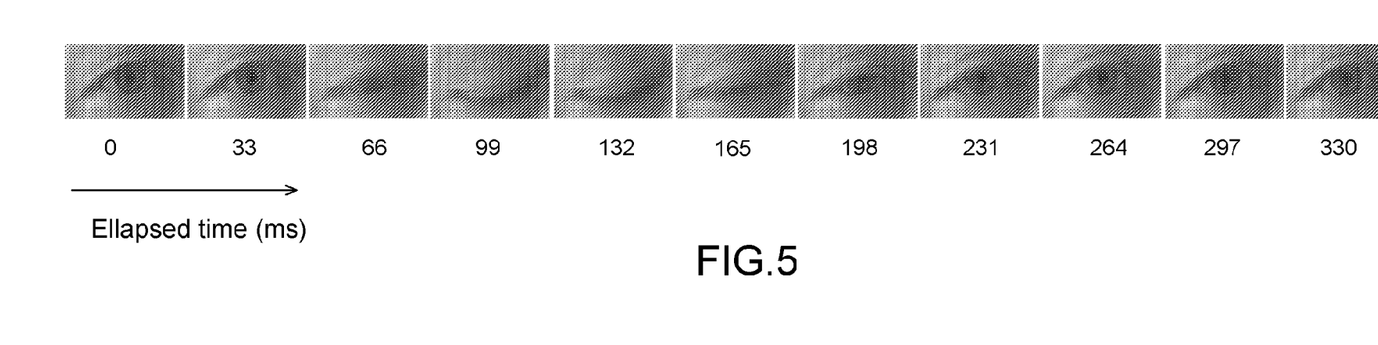
FIG. 5, pictures illustrating an eyelid closing of a user.

Eyelid blinking can be decomposed in several phases. The eyelid is closing, the eyelid is closed, the eyelid is opening. FIG. 5 shows an example of a typical eyelid closing event, captured with an ordinary video camera (30 frames/s). It can be seen on FIG. 5 that the eyelid is closed for typically 50 ms, which is more than needed to proceed to the polarization reversal. The eyelid sensor has to be fast enough such that the polarization reversal is made as soon as possible after closing of the eyelid, and anytime before the eyelid is opened again. Thus the small shock of sudden rise of focus—induced by the polarization reversal—will be hidden to the patient, since the eye is blind when the eyelid is closed.

The second mode is also very efficient, as during an eye microsaccade the image projected on the retina is quickly changed, such that a rapid change in focus will not be noticed by the patient. The change in focus is included in the rapid change of the microsaccade itself.

A few explanations about the human eye microsaccades are given below. Microsaccades are a kind of fixational eye movement. They are small, jerk-like, involuntary eye movements, similar to miniature versions of voluntary saccades. They typically occur during prolonged visual fixation (of at least several seconds), not only in humans, but also in animals with foveal vision (primates, cats, etc.). Microsaccade amplitudes vary from 2 to 120 arcminutes. From Engbert and Mergenthaler, 2006 ("Microsaccades are triggered by low retinal image slip", Proc Natl Acad Sci USA. May 2, 2006; 103(18): 7192-7197), the microsaccades are one of the three distinct types of fixational eye movements with drift and tremor, and they "represent the fastest component with the largest amplitude (5-7) and occur at an average rate of 1 to 2 per second. The trajectory generated by fixational eye movements is rather erratic and has statistical properties of a random walk (8-10). Embedded in slower movements (drift and tremor), microsaccades are ballistic jumps (<1°) of the eye, which represent roughly linear movement epoches". From the above cited publication, one can infer that the microsaccade duration is of the order of 10 ms. According to Møller et al., 2006 ("The contribution of microsaccades and drifts in the maintenance of binocular steady fixation". F. Møller, M. L. Laursen, A. K. Sjølie, Graefe's Arch Clin Exp Ophthalmol, 2006, 244: 465-471), "These fixation eye movements have been studied in detail since 1934 and are found to be fairly consistent, with fast microsaccades (duration 25 ms; amplitude 0.22°-1.11°; 0.1-5 Hz) interrupted by slow drifting movements (amplitude 0.02° -0.15°) and, constantly superimposed on these movements, a high frequency (50-100 Hz), low-amplitude (0.001°-0.008°) tremor [5, 6, 20, 23, 25]."

The duration of the microsaccades (>10 ms) is thus long enough for allowing a fast detection of the start, for instance using a gyroscope, and then applying the polarization reversal before the end of the microsaccade.

It will appear natural to the man skilled in the art that the two modes can be mixed (eyelid and microsaccades). Further, other forms of eye motion than microsaccades may be used, that will trigger the polarization reversal, as long as these eye motions are fast enough.

Figures 6, 7:
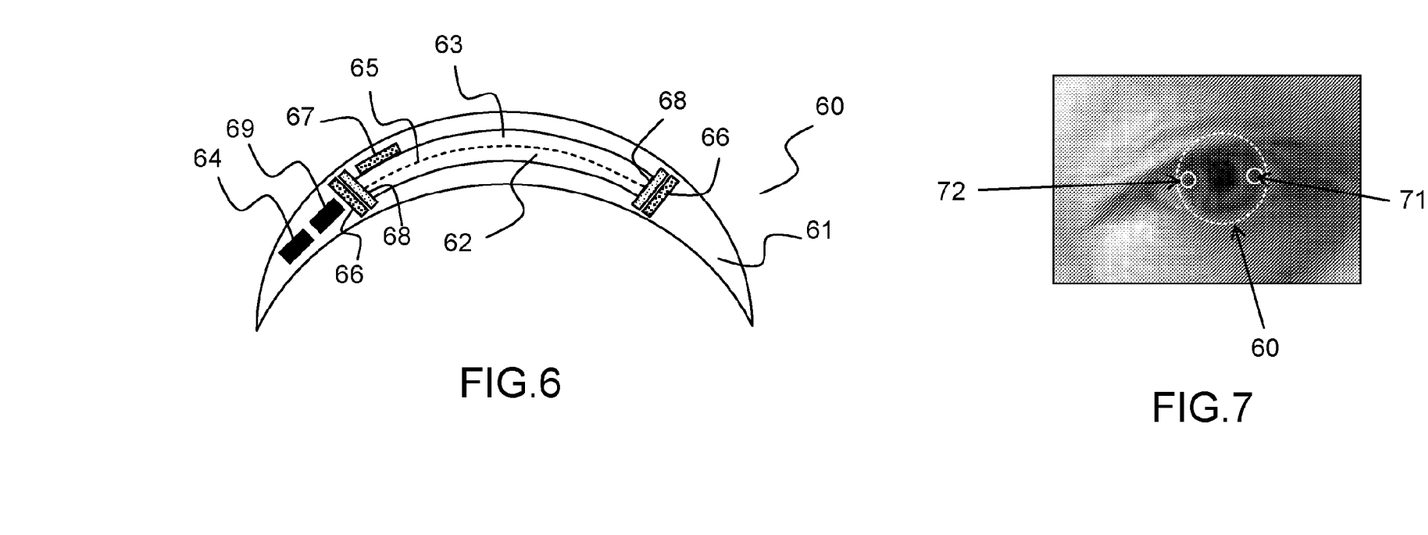
FIG. 6, an example of the internal structure of an active contact lens as shown on FIG. 4.
FIG. 7, an example of an active contact lens as shown on FIG. 6 placed on the eye of a patient.

FIG. 6 shows a possible internal structure of an active contact lens 50 adapted for an ophthalmic device as shown on FIG. 4. The active contact lens 60 comprises an electrowetting-based active liquid lens with a polymer envelope 61 containing the two transparent non miscible liquids 62, 63 forming the liquid/liquid interface 65. One of the liquids is conducting electricity, the other one is electrically insulating. As previously described with reference to FIG. 2, two electrodes 66 and 67 are arranged for electrowetting actuation. In the example of FIG. 6, the first electrode 66 has a ring shape and is covered with a thin insulator film 68. The second electrode 67 is in direct contact with the conducting liquid 63. The described device may embed all electronic components needed, including a power supply 64 for a controller and a driver (referenced 69 on FIG. 6) for the liquid lens. The packaging of the lens should be made from a transparent material which is porous to oxygen, as this is essential for contact lenses. Nevertheless, as these materials are also porous for water, there might be an evaporation of water outside from the lens, thus requiring a disposable usage. In case of intraocular implants, materials for the packaging would further need to be biocompatible, as for example hydrogels hydrophilic/hydrophobic acrylic, or silicone.

FIG. 7 shows a side view of an eye. The eyelid is open. The active contact lens 60 may correct the focus in real time, for instance using a small range meter 72, either based on ultrasonic echo, or based on infrared beams for example. The range meter measures the distance of the object in front of the eye, from 25 cm to a few meters. A controller inside the contact lens calculates the voltage to be applied to the electrowetting cell (liquid lens), and then applies the DC voltage suitable to obtain the good focus for the patient at any time. The patient has thus a good vision for near vision as well as for far vision. Another part of the controller, or another electronic circuit, may detect from the eyelid sensor 71 whether the eyelid is open or closed. As soon as the eyelid sensor detects an eyelid closing event, the controller may induce a reversal of the polarization of the DC voltage to be applied to the liquid lens.

The eyelid sensor can be a simple photodiode, which will detect low light when the eyelid is closed, or a physical contact sensor sensing the contact of the eyelid, or all other possible sensor.

The range-meter sensor may be an ultrasonic echo sensor, or devices based on infrared diode or laser light. In some other embodiments, as for example in ophthalmic implant embodiments, the distance information can be given by pressure sensors which are located at the outside of the eye, under the muscles which are controlling the convergence (see for instance patent WO 2004/004605 A1, Dr François MICHEL). As disclosed in the prior art from Toyomi Fujita et al., the distance measuring device in case of eyeglasses can also be based on the observation of the pupil convergence between the two eyes.

When polarization reversal is achieved during a microsaccade, the eyelid sensor may be replaced by a small gyroscope (e.g. MEMS devices), which detects the rotational movement of the eye. The angular velocities of the order of 100°/s which are typical of the eye microsaccades are easily measured by such sensors.

Polarization reversal may be done (in both eyelid or microsaccades cases) by using a classical H-bridge electronic structure, using 4 FET transistors, or any inverting electronic relay system.

The example as described on FIGS. 4, 6 and 7 shows the particular embodiment of a contact lens, but it is clear that the invention equally applies to all form of lenses: implants for cataract surgery (also called ophthalmic implants or crystalline implants), variable contact lenses and even variable spectacles.

Figure 8:
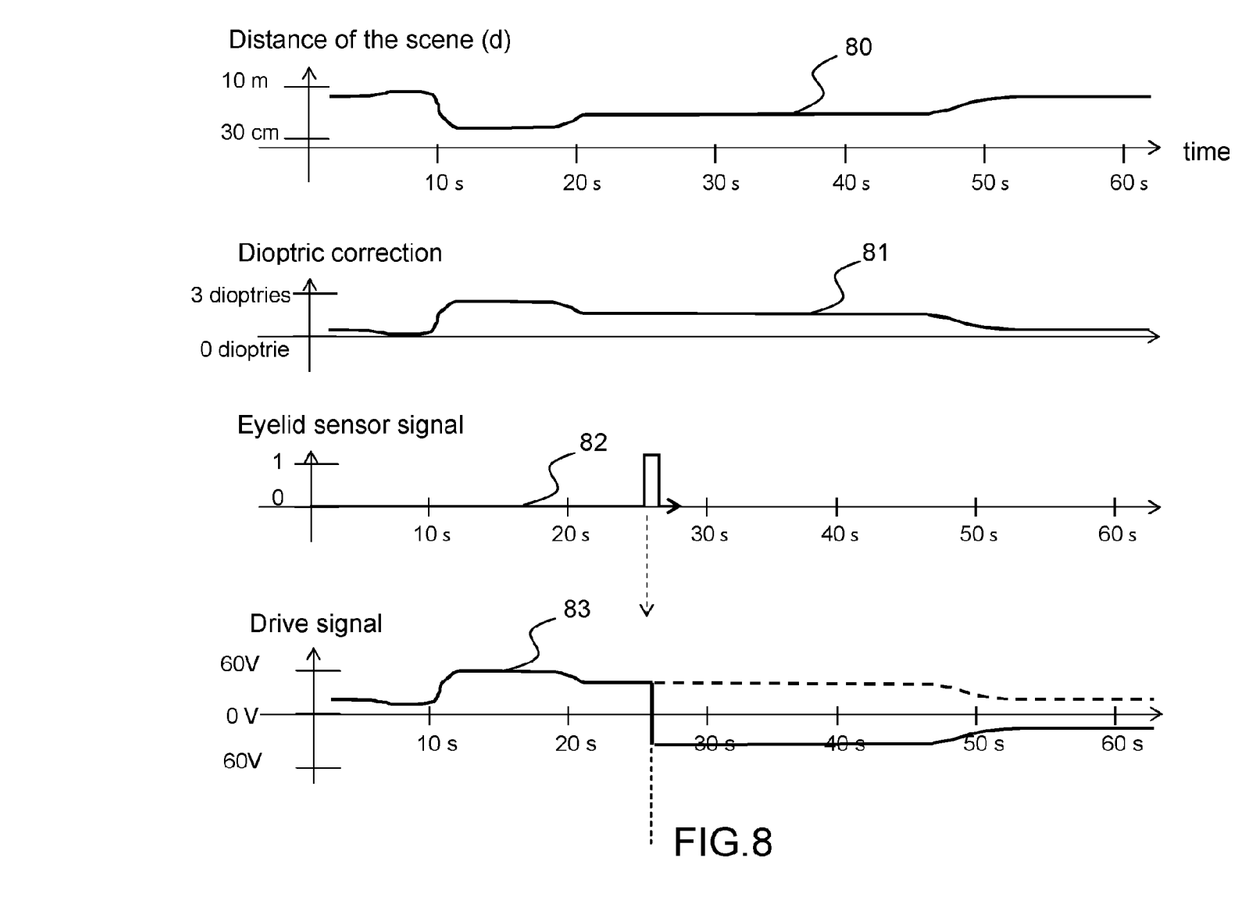
FIG. 8, diagrams illustrating according to an example the drive signal applied to the active lens as function of time and according to the distance of the scene and the eyelid closing.

FIG. 8 represents examples of diagrams illustrating the drive signal applied to the active lens as function of time and according to the distance of the scene and the eyelid closing event. The first curve 80 shown on the top of FIG. 8 represents the distance as measured by the range meter. As the patient is moving and looking at different objects, the range meter measures a variable distance with time. This measured distance d is converted in dioptric correction (curve 81) by the controller, which delivers a control voltage to the electrowetting liquid lens. The third curve 82 is the output of the eyelid sensor. Normally the eye is open, and for a short time the eyelid is closed. Note that on FIG. 8, the time scale is not intended to be accurate. The variation of distances observed before the eyelid event is shown on a long time scale, typically several seconds, while the pattern of the eyelid closing and reopening is typically 50 ms long. Just after the eyelid is detected to be closed, the controller triggers the polarization reversal. The fourth curve 83 corresponds to the effective voltage applied between the electrodes of the electrowetting device. The voltage is a function of the distance of the scene. For far vision, the voltage is lower as for near vision the voltage is higher. As previously described, the electrowetting effect is proportional to $V^2$, which means that the absolute value of the voltage is related to the measured distance. A low absolute value for the voltage corresponds to a far vision, whatever the sign of the voltage. As shown on the curve 83, the polarization reversal, which could produce a small shock in the image seen by the patient, happens at a time when the eye is blind because the eyelid is closed.

Although the above described embodiments (as well as the example of algorithm shown below) are relating to the case of an eyelid sensor, it will be apparent to the person skilled in the art that they may be extrapolated to other modes, as eye microsaccade for example. In this last case, the eyelid sensor may be replaced by the gyroscope information, with adapted filtering, noise removal and threshold.

Advantageously, material engineering, and particularly engineering of the insulator film and liquids, is made to achieve large time constants $\tau$ of the electrowetting effect. It usually requires insulators being resistant to charge injection. Generally, hard materials in which electric charges e.g. ions cannot penetrate easily, will be good candidates. For example using a parylene insulating layer coated with a fluoropolymer under DC voltage may lead to time constants greater than 1 s (see for example *Langmuir* 1998, 14, 1535-1538, Welters et al.). The use of fluorinated organic, or inorganic materials, or hybrid organic-inorganic materials formed by sol-gel synthesis could be of interest as well to get large time constants. Further, the electrically conducting liquid advantageously comprises a water solution with salts, preferably salts consisting of large size ions. The non conducting liquid advantageously comprises a mixture of aliphatic oils, aromatic oils, silicone oils, germane compounds. Engineering of the liquids in an electrowetting-based liquid lens is for example described in published patent application WO2007088453A1 in the name of the applicant.

Figure 9:
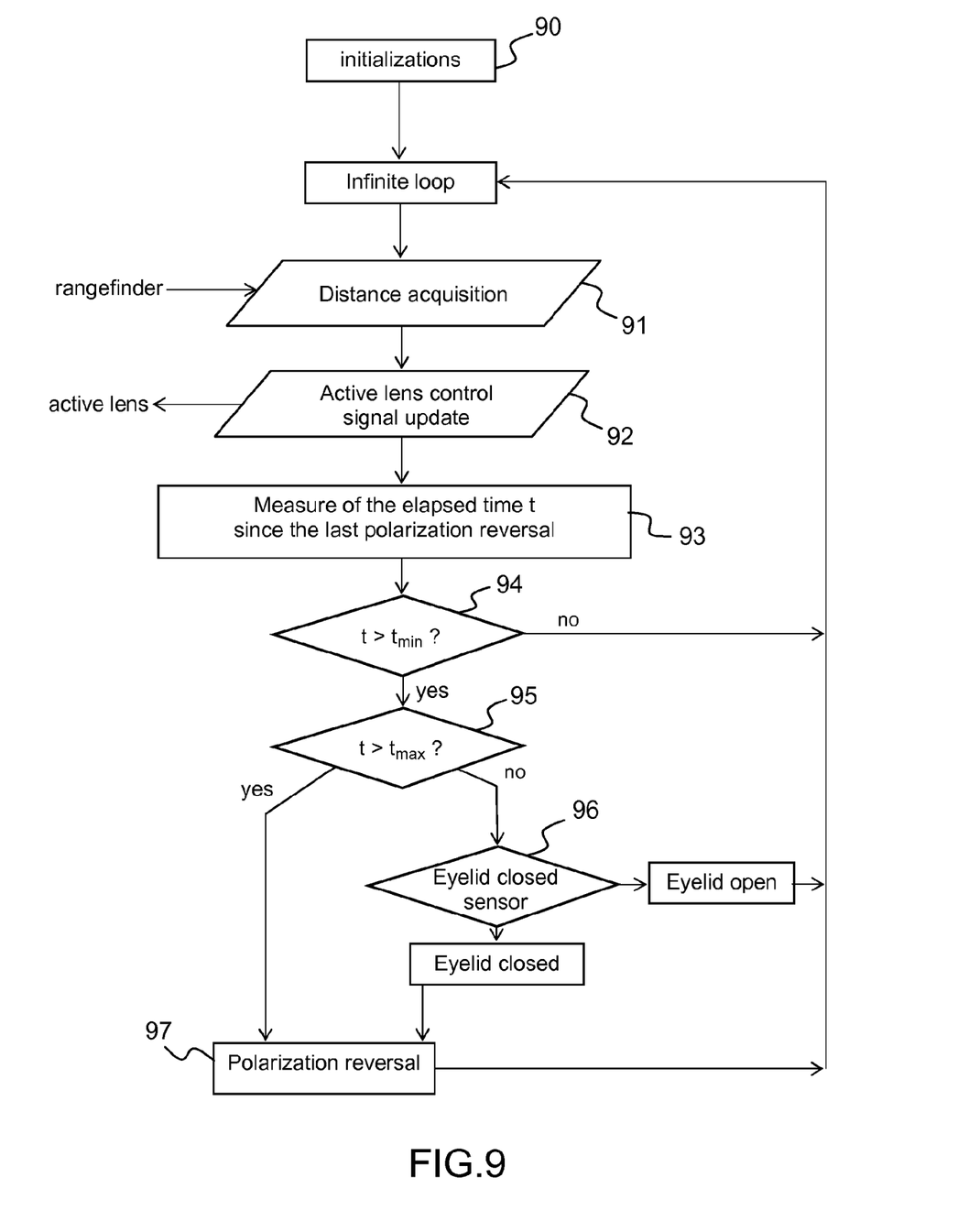
FIG. 9, a schema illustrating the method for controlling an electrically controlled focusing ophthalmic device according to a preferred embodiment of the invention.

FIG. 9 is a flowchart of a method for controlling an automatic focusing correction lens according to a preferred embodiment of the invention. In this embodiment, an infinite loop enables to have a real time correction of the automatic focusing lens as a function of the measured distance, insuring that the vision is always sharp (steps 91, 92, FIG. 9). A timer is set in order to monitor the time elapsed since the last polarization reversal (93, FIG. 9). A series of tests are implemented to ensure that the polarization reversal is done not too frequently nor too rarely. As a matter of fact, if the user blinks its eyelids too often, and if the system is reversing the polarization each time the eyelid is found closed, there will be a high power consumption, resulting in a loss of autonomy of the battery. To prevent from this effect, a first test ($t > t_{min}$) insures that if the last polarization reversal event is recent, there is no need for another polarization reversal (94, FIG. 9). The value of $t_{min}$ is determined by the maximum power consumption that can be tolerated by the device. Typically $t_{min}$ could be of the order of 1 s to 5 s. On the opposite, if the eyelid closes too rarely, there is a risk that the electrowetting effect has lost too much of its efficiency since the last polarization reversal. A second test ($t > t_{max}$) insures that there will be an immediate polarization reversal event after a given time $t_{max}$ has elapsed (95, FIG. 9). The value of $t_{max}$ should be smaller than the time constant $\tau$ of the electrowetting effect, typically about one minute, in order to have a residual shock perturbation when the polarization is reversed as small as possible. In the case where the elapsed time since the last polarization reversal is comprised between $t_{min}$ and $t_{max}$, a third test (96, FIG. 9) will monitor the closing of the eyelid; if the eyelid is closed, the polarization reversal event happens (97).

In the case of a control of the polarization reversal using eye microsaccades, there might be some obvious differences, linked to the signal processing of the gyroscope and threshold of the angular speed information, in order to deliver reliable information to the control system for polarization reversal proceeding.

The algorithm as shown on FIG. 9 has been described for a single eye control. In case of an electrically controlled focusing ophthalmic device being an intraocular implant or a contact lens, independent controls of the devices for each of the two eyes would be the easiest mode control. However, it could be advantageous to synchronize both controls, requiring a communication between the controllers of the devices of each of the two eyes. In case of eyeglasses, a single controller and a single distance measuring device could be implemented, enabling synchronization of the controls for both active lenses of the eyeglasses.

While the invention has been described with respect to a limited number of embodiments, those skilled in the art, having benefit of this disclosure, will appreciate that other embodiments can be devised which do not depart from the scope of the invention as disclosed herein. In particular, the invention is also applicable to eye testing and eye diagnosis apparatus like phoropters, refractometers, microscopes for retina examination, or simple eye examiner tools. In that case it could be uncomfortable for the patient to have the polarization reversal shocks, such that the principle of this invention could be useful, for instance for portable devices but not only. Accordingly, the scope of the invention should be limited only by the attached claims.

The invention claimed is:

1. A method for controlling an electrically controlled focusing ophthalmic device worn by a user, said device comprising at least one active lens comprising a liquid/liquid interface movable by electrowetting under the application of a voltage, said method comprising:
    applying a DC voltage to said active lens, the amplitude of the voltage being a function of the desired focusing of the ophthalmic device;
    detecting a microsaccade and/or eyelid closing event of the user; and
    reversing the polarization of the DC voltage during said microsaccade and/or eyelid closing event.

2. The method according to claim 1, further comprising:
    measuring the elapsed time (t) since the last polarization reversal of the voltage;
    reversing the polarization of the DC voltage only when said elapsed time is larger than a given first value ($t_{min}$).

3. The method according to claim 2, wherein said first value ($t_{min}$) is comprised between 1 s and 5 s.

4. The method according to claim 3, further comprising:
    reversing the polarization of the DC voltage during the next detected microsaccade or eyelid closing event of the user when said elapsed time (t) is larger than said first value ($t_{min}$) and smaller than a given second value ($t_{max}$);
    reversing the polarization of the DC voltage as soon as said elapsed time is larger than said second value ($t_{max}$).

5. The method according to claim 4, wherein said second value ($t_{max}$) is comprised between 10 s and 2 min.

6. The method according to claim 1, further comprising measuring the distance of an object the user is looking at to determine the desired focusing.

7. An electrically controlled focusing ophthalmic device to be worn by a user, comprising:
    at least one active liquid lens comprising a liquid/liquid interface movable by electrowetting under the application of a voltage;
    a driver for applying a DC voltage to said active liquid lens, the amplitude of the voltage to be applied being a function of the desired focusing;
    a sensor for detecting eyelid closing events and/or microsaccades of the user; and
    a controller for synchronizing said sensor and the driver, such that the driver may reverse the polarization of the DC voltage during a microsaccade and/or an eyelid closing event of the user.

8. The ophthalmic device of claim 7, further comprising a device for measuring the distance of an object the user is looking at, the desired focusing being function of the measured distance.

9. The ophthalmic device of claim 7, wherein the controller is further adapted for measuring the elapsed time since the last polarization reversal.

10. The ophthalmic device of claim 7, wherein the active liquid lens comprises:
    a chamber containing two transparent non miscible liquids forming said liquid/liquid interface, a first electrically conducting liquid and a second non conducting liquid,
    a first electrode covered with an insulator film and a second electrode in contact with said electrically conducting liquid, the DC voltage being applied to said electrodes.

11. The ophthalmic device of claim 7, wherein the time constant ($\tau$) of the electrowetting effect is larger that 1 s.

12. The ophthalmic device of claim 7, said device being an intra ocular implant or a contact lens.

13. The ophthalmic device of claim 7, said device being a pair of eyeglasses comprising two active liquid lenses and a driver for each active liquid lens, the controller further ensuring the synchronization between said sensor and the drivers.

* * * * *

UNITED STATES PATENT AND TRADEMARK OFFICE
CERTIFICATE OF CORRECTION

| | | |
|---|---|---|
| PATENT NO. | : 8,545,555 B2 | Page 1 of 1 |
| APPLICATION NO. | : 13/513678 | |
| DATED | : October 1, 2013 | |
| INVENTOR(S) | : Bruno Berge | |

It is certified that error appears in the above-identified patent and that said Letters Patent is hereby corrected as shown below:

On the title page:

Item (75) the city is read as "Lyon<u>s</u>" and should be read as -- Lyon --.

On the title page:

Insert Item -- (60) Related U.S. Application Data

Provisional application No. 61/266,712, filed on December 4, 2009 --.

Signed and Sealed this
Eighteenth Day of February, 2014

Michelle K. Lee
*Deputy Director of the United States Patent and Trademark Office*